(12) United States Patent
Cardonha et al.

(10) Patent No.: US 11,152,107 B2
(45) Date of Patent: Oct. 19, 2021

(54) SYSTEM, METHOD AND COMPUTER PROGRAM PRODUCT FOR DISPATCHING OF MEDICAL EMERGENCIES AND WAIT TIME CONTROL

(71) Applicant: International Business Machines Corporation, Armonk, NY (US)

(72) Inventors: Carlos Henrique Cardonha, São Paulo (BR); Jorge Luis Guevara Diaz, São Paulo (BR); Bernardo Nunes Goncalves, São Paulo (BR); Marisa A. Vasconcelos, São Paulo (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 429 days.

(21) Appl. No.: 15/279,632

(22) Filed: Sep. 29, 2016

(65) Prior Publication Data
US 2018/0089377 A1   Mar. 29, 2018

(51) Int. Cl.
*G16H 40/20*   (2018.01)

(52) U.S. Cl.
CPC ................... *G16H 40/20* (2018.01)

(58) Field of Classification Search
CPC ........................................................ G16H 40/20
See application file for complete search history.

(56) References Cited

U.S. PATENT DOCUMENTS

| | | | |
|---|---|---|---|
| 6,735,569 B1 * | 5/2004 | Wizig | G06Q 30/02 705/4 |
| 7,106,835 B2 | 9/2006 | Saalsaa | |
| 8,060,500 B1 * | 11/2011 | Fitch | G16H 40/20 707/724 |
| 8,484,048 B2 * | 7/2013 | Halsted | G06Q 50/22 705/3 |
| 8,712,793 B2 | 4/2014 | Jones et al. | |
| 9,082,156 B2 | 7/2015 | Matos | |
| 2004/0138924 A1 * | 7/2004 | Pristine | G16H 10/20 705/2 |
| 2008/0243545 A1 | 10/2008 | D'Ambrosia et al. | |
| 2009/0198733 A1 * | 8/2009 | Gounares | G06F 19/3418 |

(Continued)

FOREIGN PATENT DOCUMENTS

JP    2002-366657 A    12/2002

OTHER PUBLICATIONS

Herbert Alexander Baier Saip and Claudio Leonardo Lucchesi, "Matching Algorithms for Bipartite Graphs", Mar. 1993, 21 pages (Year: 1993).*

(Continued)

*Primary Examiner* — Janice A Mooneyham
*Assistant Examiner* — Steven G Sanghera
(74) *Attorney, Agent, or Firm* — Joseph Petrokaitis, Esq.; McGinn I.P. Law Group, PLLC.

(57) ABSTRACT

A wait time control method, system, and computer program product, includes extracting wait times for treatment at emergency facilities and routing times to the emergency facilities based on an emergency request and assigning a patient to an emergency facility by calculating a minimal treatment time for the patient comprising a minimum combined time of a wait time at the emergency facility and a routing time to the emergency facility from a location of the emergency request.

3 Claims, 4 Drawing Sheets

(56) References Cited

U.S. PATENT DOCUMENTS

| | | | | |
|---|---|---|---|---|
| 2011/0054946 A1* | 3/2011 | Coulter | ............... | G06Q 10/06 |
| | | | | 705/3 |
| 2012/0203564 A1 | 8/2012 | Myr | | |
| 2013/0035581 A1 | 2/2013 | Vesto | | |
| 2013/0262133 A1 | 10/2013 | Rodriguez et al. | | |
| 2014/0249850 A1* | 9/2014 | Woodson | ............... | G16H 15/00 |
| | | | | 705/3 |
| 2015/0106119 A1* | 4/2015 | McCafferty | ............ | G06Q 50/24 |
| | | | | 705/3 |
| 2018/0068078 A1* | 3/2018 | Barthell | ............... | G06N 20/00 |

OTHER PUBLICATIONS

Hernert Alexander Baier Saip and Claudio Leonardo Lucchesi, "Matching Algorithms for Bipartite Graphs", Mar. 1993, 21 pages (Year: 1993).*

Hemert Alexander Baier Saip and Claudio Leonardo Lucchesi, "Matching Algorithms for Bipartite Graphs", Mar. 1993, 21 pages (Year: 1993).*

Mel, et al. "The NIST Definition of Cloud Computing". Recommendations of the National Institute of Standards and Technology. Nov. 16, 2015.

Ho, Chen-Shie, et al. "Study of patient waiting time in the emergence department: an example of a medical center in New Taipei County, Taiwan". Applied Mechanics and Materials vols. 519-520, pp. 1581-1584. Feb. 6, 2014.

* cited by examiner

SYSTEM, METHOD AND COMPUTER PROGRAM PRODUCT FOR DISPATCHING OF MEDICAL EMERGENCIES AND WAIT TIME CONTROL

BACKGROUND

The present invention relates generally to a wait time control method, and more particularly, but not by way of limitation, to a system, method, and computer program product for dispatching of medical emergencies for a minimization of a total time between dispatch and treatment. "Dispatch" means when the emergency vehicle or emergency station receives a notification of the medical emergency.

The efficacy of treatments ministered for medical emergencies is frequently inversely proportional to the amount of time separating the event and the beginning of the treatment. The "waiting time" for individuals needing emergency care is typically given by the sum of the transportation time (e.g., from the individual's home to a suitable hospital or ambulance station) with the waiting time in the treatment location.

Conventional techniques have considered monitoring traffic patterns to route emergency vehicles to emergency facilities.

However, there is a technical problem in the conventional techniques do not consider an optimization of a total time between dispatch and treatment.

SUMMARY

In view of the at least one technical problem in the conventional techniques, the inventors have considered a technical solution to the technical problem by creating an integrated routing plan of medical emergencies to emergency facilities, aiming at the minimization of the time each individual has to wait in order to start being treated in the emergency vehicle.

In an exemplary embodiment, the present invention can provide a computer-implemented wait time control method, the method includes extracting wait times for treatment at emergency facilities and routing times to the emergency facilities based on an emergency request and assigning a patient to an emergency facility by calculating a minimal treatment time for the patient comprising a minimum combined time of a wait time at the emergency facility and a routing time to the emergency facility from a location of the emergency request.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
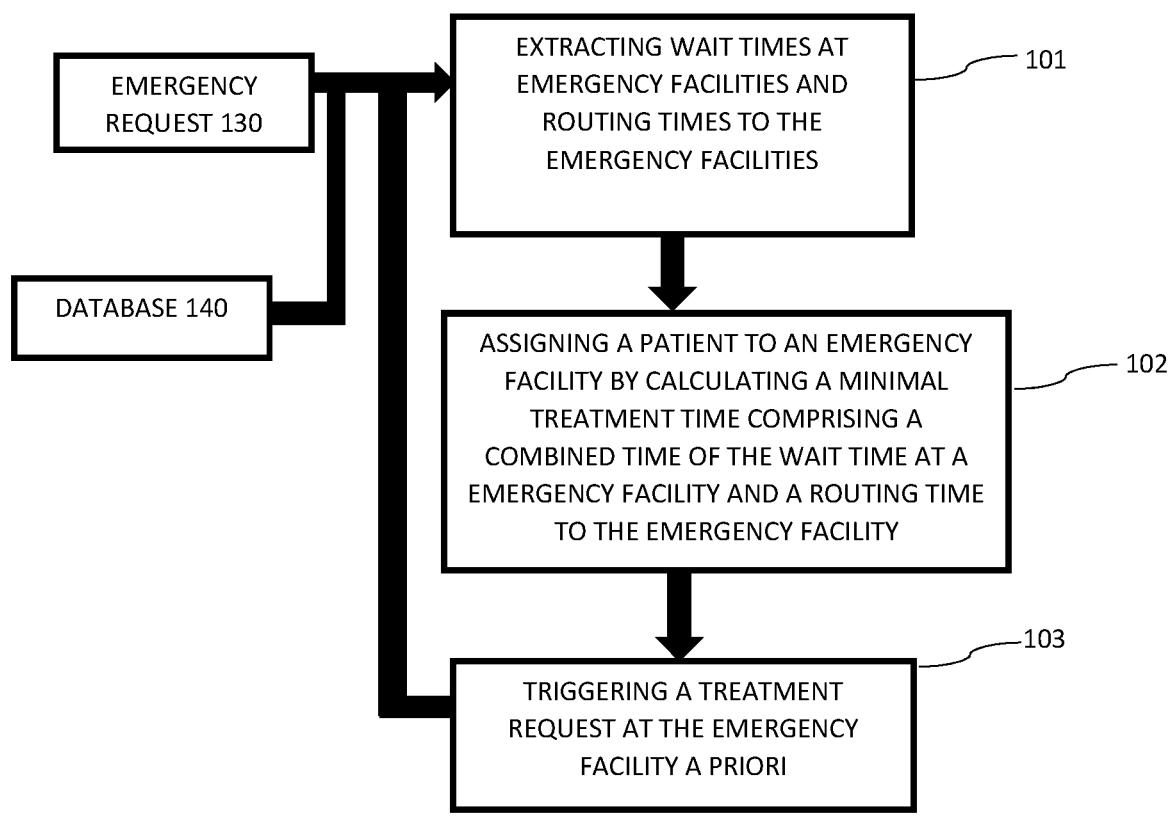
FIG. 1 exemplarily shows a high-level flow chart for a wait time control method 100.

The invention will now be described with reference to FIG. 1-4, in which like reference numerals refer to like parts throughout. It is emphasized that, according to common practice, the various features of the drawing are not necessarily to scale. On the contrary, the dimensions of the various features can be arbitrarily expanded or reduced for clarity.

With reference now to the example depicted in FIG. 1, the wait time control method 100 includes various steps to extract wait times at emergency facilities and routing times to the emergency facilities to assign a patient to an emergency facility by calculating a minimal combined time of the routing times (i.e., elapsed time from when the patient is picked up by the emergency vehicle to when the vehicle arrives at the emergency facility) and the wait time at the emergency facility such that the patient can receive a fastest possible treatment time. As shown in at least FIG. 2, one or more computers of a computer system 12 according to an embodiment of the present invention can include a memory 28 having instructions stored in a storage system to perform the steps of FIG. 1.

Although one or more embodiments (see e.g., FIGS. 2-4) may be implemented in a cloud environment 50 (see e.g., FIG. 3), it is nonetheless understood that the present invention can be implemented outside of the cloud environment.

In step 101, wait times at emergency facilities and routing times to the emergency facilities are extracted based on an emergency request 130 and from a database 140. That is requests for medical emergencies from individuals are received, emergency facilities waiting times are extracted and potential routes from a location (i.e., a patient's home, workplace, etc.) of the emergency request 130 to the emergency facilities are extracted using real-time information about traffic conditions, weather, etc. in order to determine all potential routes to the emergency facilities. It is noted that the database 140 includes information for a dispatching center including a list of hospitals and the "capabilities" of each hospital (i.e., which types of emergency services each hospital is able to provide). For example, if the emergency request is for a gun-shot wound, a trauma center may be required at the emergency facility in order to provide treatment.

Thus, in step 101, the wait times are extracted only for emergency facilities that include a trauma center. In other words, only wait times are extracted for emergency facilities that are capable of treatment. In some embodiments, low-level walk-in medical clinics or health stores can be included in the list of potential emergency facilities. For example, if the emergency request 130 comprises an allergic reaction to a bee sting, the quickest wait time may be at a local pharmacy or health store in the form of over the counter medicine.

Based on the list of capable emergency facilities, a plurality of routes (i.e., via a route creation interface) are extracted to each of the emergency facilities. The routes are extracted while weighing traffic conditions, weather, congestion created by emergency vehicles, etc.

Therefore, in step 101, a plurality of routing times (e.g., the time it takes to travel from a location of the emergency request 130 to the emergency facilities) and the wait times at the emergency facilities are extracted.

Alternatively, a set of eligible users can be registered in the database 140. Optionally, this set of potential users may be restricted (e.g., to clients of a medical insurance company, who would offer this invention as a service).

A user may use an application deployed on a smartphone, in which they indicate the type of the emergency. The individual's pick-up location can be either automatically extracted (e.g., from the smartphone) or explicitly informed by the person (e.g., via an emergency call). Alternatively, the person may indicate whether she needs an ambulance or if someone will drive her to the hospital chosen by the system.

In step 102, a patient is assigned to a capable emergency facility by calculating a treatment time comprising a combined time of the wait time at a capable emergency facility and a routing time to the capable emergency facility. In other words, a patient is assigned to the emergency facility in which the time to travel to the emergency facility and the time to wait at the emergency facility before receiving treatment is the smallest wait time of all the potential routes, emergency facilities, and wait times thereof.

That is, assignment decisions of the patient are calculated in a way that the weighted sum of the total waiting times for all individuals sending an emergency request is minimized. The total waiting time of a service request is the time between the submission of the emergency request 130 (or alternatively the time of pick-up) and the beginning of the treatment at the hospital. In other words, the total waiting time is the sum of the travel time (estimated time to transport an individual from the service request location to a suitable hospital) with the hospital waiting time (time an individual has to wait once she arrives at the hospital).

In step 102, the minimal time is calculated by taking into account the commuting time from the individual's location to the hospital and the waiting time at the hospital's queue. To calculate the minimal route time, the information describing the traffic conditions of the area (which can be obtained from Google Maps, for example) is taken into account, whereas the second minimization calculation combined with the first minimization relies on the information provided by the hospitals. As discussed above, the feasibility of treatment, that is, a patient can only be assigned to a suitable hospital, which is a hospital that can deal with (i.e., treat) the medical emergency is factored in to filter out particular emergency facilities.

In step 103, a treatment request at the emergency facility is triggered a priori (e.g., while the patient is in route to the emergency facility) according to the patient being assigned to the emergency facility with the minimal treatment time. That is, when the patient is assigned to a given emergency facility, a communication channel is established in order to facilitate the information exchange process. With this, patients might be able to receive some treatment in advance and to provide bureaucratic information (e.g., filling form procedures that could otherwise increase the hospital waiting time). These elements can also be taken into account in the definition of penalties associated with delays in each scenario (e.g., if a person can receive satisfactory treatment already in the ambulance, the penalty with delays on her medical hospitalization should be smaller). Thus, the treatment request feeds back to update the wait times based on the patient potentially receiving care while in the medical transportation vehicle.

In some embodiments, the patient assignment and treatment request can move the patient up in wait times based on a severity of the medical emergency. Because different patients may have different urgency levels (e.g., a first individuals broken leg vs. a second individuals heart attack, individuals' conditions), different weights may be given to the waiting times of different individuals; that is, higher penalties are assigned to more critical scenarios. For example, in step 101, the current wait times are extracted at the emergency facilities but based on the severity of the emergency request and the known number of patients in queue at the emergency facility, the wait time can be factored against a predetermined severity factor to reduce the actual wait time the patient will have. That is, if the current wait time at the emergency facility is forty minutes but each patient in queue (e.g., as put in queue a priori by the treatment request) has a severity level of their treatment less than the current medical emergency, the weight time is factored down by a predetermined factor to reduce the estimated wait time at that facility when determining which medical facility to assign the patient to. In other words, if the patient's medical emergency was less severe than everyone's medical emergency in queue, the wait time of forty minutes would be the minimal time at that medical facility. However, if the patient has a life threatening medical emergency and needs instant treatment, the wait time could be factored down to zero minutes (i.e., instant treatment upon arrival) such that the minimal treatment time essentially comprises the route time.

In some embodiments, people who have been waiting for a certain amount of time in the queue already should not be put back in the queue (avoiding thus "starvation" of simple treatments). In another embodiment, the queues might be completely reorganized based on severity levels. In the second case, though, the system also takes into account that certain assignments of individuals to treatment centers are fixed and that their waiting times should consider also the time they already spent since they triggered the treatment request.

In some embodiments, the minimal treatment time is calculated by formulating the minimization of the route time and the wait time as a weighted bipartite assignment problem in which a set of edges connecting vertices from a set "P" (e.g., each vertex of P represents a patient) to vertices belonging to set "H" (e.g., each vertex of H represents a time-slot in a hospital) such that the each vertex appears at most once (i.e., each patient is assigned to a single time-slot in a single hospital, and no time-slot is assigned more than once) and the sum of the weights of the selected edges is maximum. The weight of each edge is given by the product of the inverse of the total waiting time associated with this assignment, which increases with shorter total waiting times, multiplied by some factor that varies according to the criticality level of the incident (e.g., the factor may be "2" for a broken leg and "10" for a heart attack).

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 2:
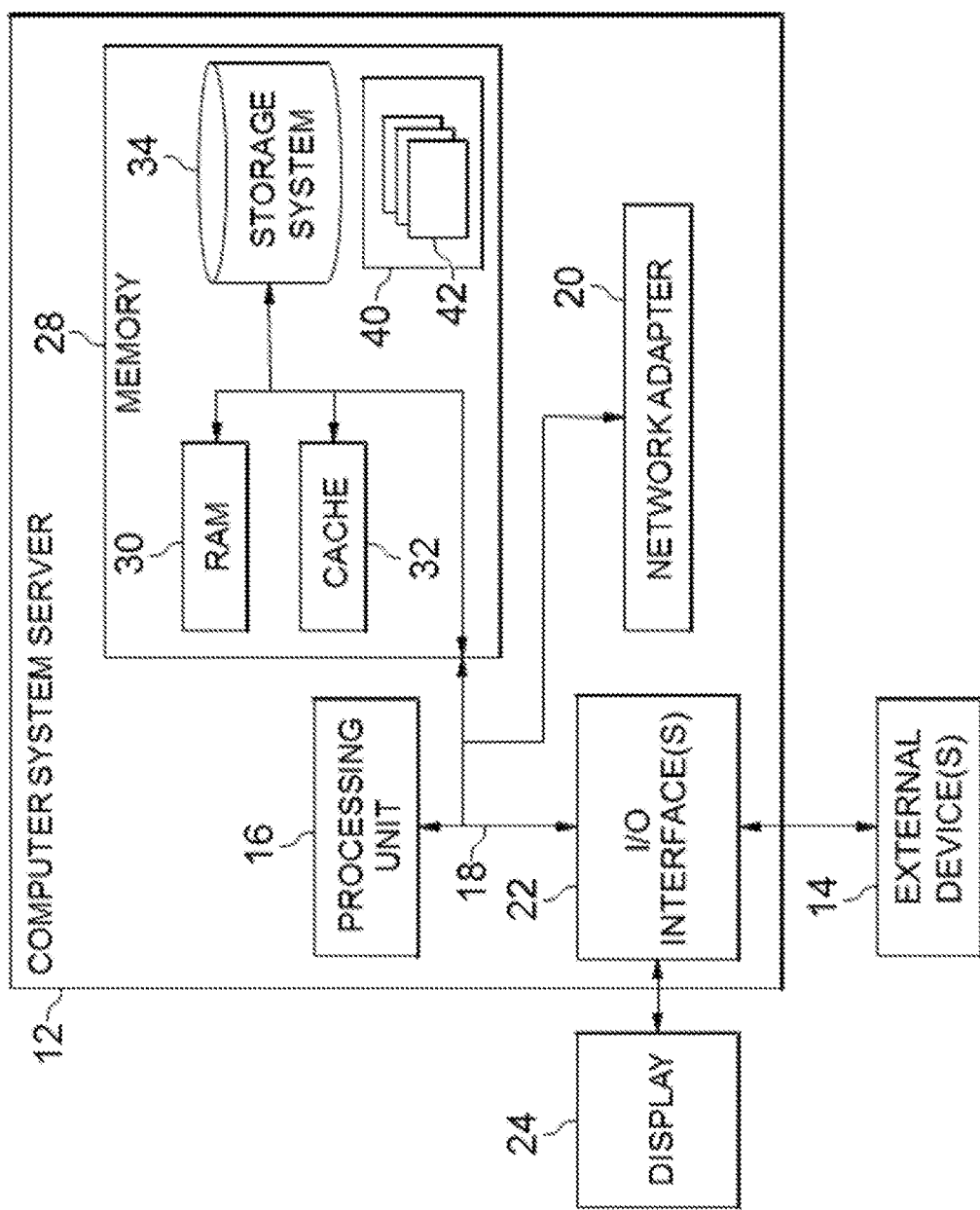
FIG. 2 depicts a cloud computing node according to an embodiment of the present invention.

Referring now to FIG. 2, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring again to FIG. 2, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 3:
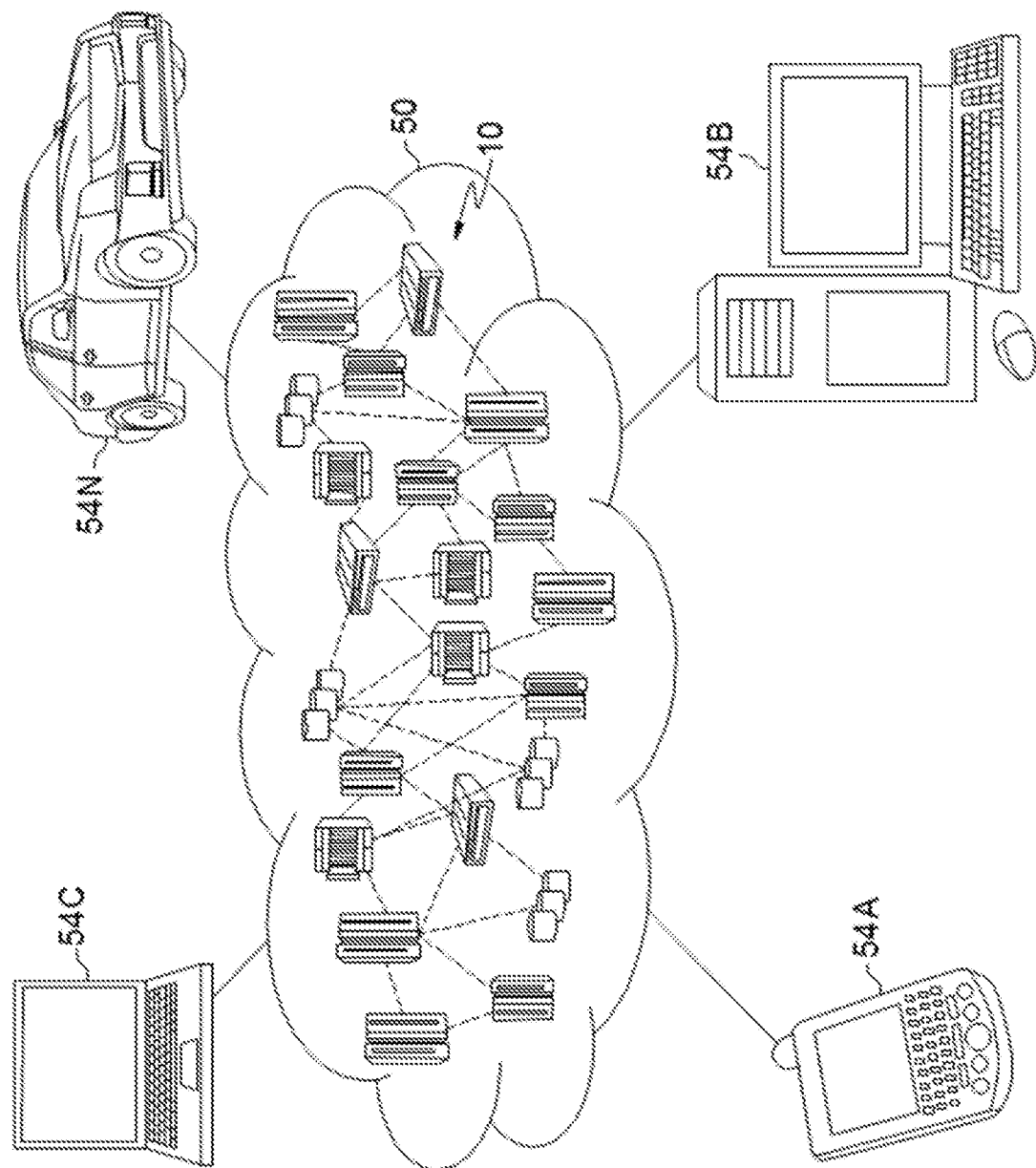
FIG. 3 depicts a cloud computing environment according to an embodiment of the present invention.

Referring now to FIG. 3, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 3 are intended to be illustrative only and that computing nodes 10 and cloud computing environment 50 can communicate with any type of computerized circuit over any type of network and/or network addressable connection (e.g., using a web browser).

Figure 4:
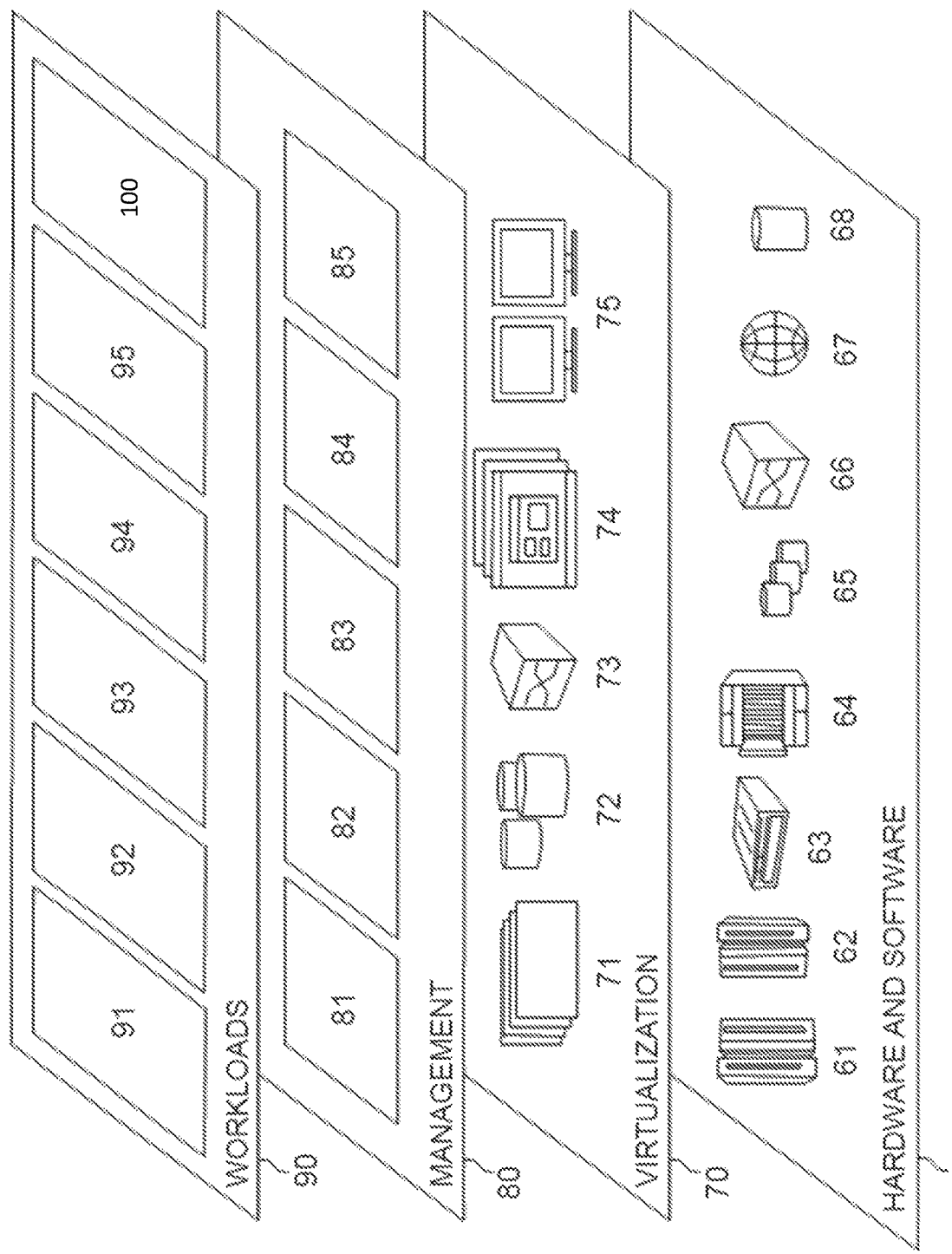
FIG. 4 depicts abstraction model layers according to an embodiment of the present invention.

Referring now to FIG. 4, an exemplary set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the wait time control method 100.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented wait time control method that interacts with a cloud computing infrastructure to optimize wait times and routing times, the method comprising:

providing a database connected to a dispatching center; said database comprising information on a plurality of emergency facilities, capabilities of each emergency facility, and restricted lists of acceptable patients for each emergency facility, said database connected to the cloud computing infrastructure which connects the plurality of emergency facilities and the dispatching center via the infrastructure;

receiving an emergency request for a patient;

extracting from the database wait times for treatment at emergency facilities that are capable of treating the patient and extracting potential routes and routing times to the facilities based on the weighted conditions at the time the emergency request is made;

assigning, via a cloud on-demand self-service running on an application on a graphical-user interface that communicates with the cloud computing infrastructure, a patient who is on the restricted list of acceptable patients to the emergency facility at the time of the emergency request by calculating a minimal treatment time for the patient comprising a minimum combined time of a wait time at the emergency facility and a routing time to the emergency facility from a location of the emergency request, and assigning the patient to the emergency facility having the minimum combined time with treatment capability for the emergency request based on the capability of each emergency facility;

determining wait times comprises factoring the severity of the emergency request and the number of patients in a queue at the emergency facility;

cross-checking assigned emergency facilities with the necessary capabilities to treat the patient from the database and confirming the emergency facility having the capabilities for the emergency request has combined minimum wait time, routing time and treatment capability;

facilitating information exchange with the emergency facility, via the cloud computing infrastructure after assigning the patient to the emergency facility while the patient is in-route to the emergency facility;

iteratively re-computing the minimal treatment time at a second time for each new emergency request for a new patient based on new emergency treatment request after the minimal treatment time was calculated at the time of the emergency request;

wherein the treatment request feeds back to update the wait times based on the patient potentially receiving care while in the medical transportation vehicle;

wherein the assigning re-assigns the patient and each new patient based on the recomputed minimal treatment time considering the severity level of the patient and the number of patients in each queue; wherein the minimal treatment time is optimized for the patient by the assigning a weighted sum of the wait times of all patients that requested medical services, wherein the minimal treatment time is calculated by using a weighted bipartite assignment having a set of edges connecting vertices from a set of patients to vertices belonging to a set of time-slots in the emergency facilities such that each vertex appears at most once and a sum of the weights of selected edges is a maximum, and wherein the routing time starts at the time of the emergency request, further comprising triggering, via the cloud on-demand self-service running on the application on the graphical-user interface that communicates with the cloud computing environment, a treatment request at the emergency facility to place the patient in a wait time queue a priori according to the patient being assigned to the emergency facility with the minimal treatment time, wherein the database including the information further including a second restricted list of authorized patients for a medical insurance accepted at the emergency facilities, the second restricted list being a subset of the first restricted list, wherein the assigning calculates the routing time to the emergency facility according to traffic data and a minimization of a time to reach the emergency facility based on the traffic data, wherein the wait time at the emergency facility used in the calculating the minimal treatment time is adjusted according to a weighted severity of the emergency request; and creating and assigning the patient into an integrated routing plan to an appropriate emergency facility by feeding the data collected from the database, the facilities, traffic conditions, routes into an algorithm which assigns each patient and integrated routing plan to an appropriate emergency facility with the best treatment time.

2. A computer program product for wait time control that interacts with a could computing infrastructure to optimize wait times and routing times, the computer program product comprising a computer readable storage medium having program instructions embodied therewith, the program instructions executable by a computer to cause the computer to perform:

providing a database connected to a dispatching center; said database comprising information on a plurality of emergency facilities, capabilities of each emergency facility, and restricted lists of acceptable patients for each emergency facility, said database connected to the cloud computing infrastructure which connects the plurality of emergency facilities and the dispatching center via the infrastructure;

receiving an emergency request for a patient;

extracting from the database wait times for treatment at emergency facilities that are capable of treating the patient and extracting potential routes and routing times to the facilities based on the weighted conditions at the time the emergency request is made;

assigning, via a cloud on-demand self-service running on an application on a graphical-user interface that communicates with the cloud computing infrastructure, a patient who is on the restricted list of acceptable patients to the emergency facility at the time of the emergency request by calculating a minimal treatment time for the patient comprising a minimum combined time of a wait time at the emergency facility and a routing time to the emergency facility from a location of the emergency request, and assigning the patient to the emergency facility having the minimum combined time with treatment capability for the emergency request based on the capability of each emergency facility;

determining wait times comprises factoring the severity of the emergency request and the number of patients in a queue at the emergency facility;

cross-checking assigned emergency facilities with the necessary capabilities to treat the patient from the database and confirming the emergency facility having the capabilities for the emergency request has combined minimum wait time, routing time and treatment capability;

facilitating information exchange with the emergency facility, via the cloud computing infrastructure after assigning the patient to the emergency facility while the patient is in-route to the emergency facility;

iteratively re-computing the minimal treatment time at a second time for each new emergency request for a new patient based on new emergency treatment request after the minimal treatment time was calculated at the time of the emergency request;

wherein the treatment request feeds back to update the wait times based on the patient potentially receiving care while in the medical transportation vehicle;

wherein the assigning re-assigns the patient and each new patient based on the recomputed minimal treatment time considering the severity level of the patient and the number of patients in each queue; wherein the minimal treatment time is optimized for the patient by the assigning a weighted sum of the wait times of all patients that requested medical services, wherein the minimal treatment time is calculated by using a weighted bipartite assignment having a set of edges connecting vertices from a set of patients to vertices belonging to a set of time-slots in the emergency facilities such that each vertex appears at most once and a sum of the weights of selected edges is a maximum, and wherein the routing time starts at the time of the emergency request, further comprising triggering, via the cloud on-demand self-service running on the application on the graphical-user interface that communicates with the cloud computing environment, a treatment request at the emergency facility to place the patient in a wait time queue a priori according to the patient being assigned to the emergency facility with the minimal treatment time, wherein the database including the information further including a second restricted list of authorized patients for a medical insurance accepted at the emergency facilities, the second restricted list being a subset of the first restricted list, wherein the assigning calculates the routing time to the emergency facility according to traffic data and a minimization of a time to reach the emergency facility based on the traffic data, wherein the wait time at the emergency facility used in the calculating the minimal treatment time is adjusted according to a weighted severity of the emergency request; and creating and assigning the patient into an integrated routing plan to an appropriate emergency facility by feeding the data collected from the database, the facilities, traffic conditions, routes into an algorithm which assigns each patient and integrated routing plan to an appropriate emergency facility with the best treatment time.

3. A wait time control system that interacts with a cloud computing infrastructure to optimize wait times and routing times, said system comprising:

a processor; and a memory, the memory storing instructions to cause the processor to perform:

providing a database connected to a dispatching center; said database comprising information on a plurality of emergency facilities, capabilities of each emergency facility, and restricted lists of acceptable patients for each emergency facility, said database connected to the cloud computing infrastructure which connects the plurality of emergency facilities and the dispatching center via the infrastructure;

receiving an emergency request for a patient;

extracting from the database wait times for treatment at emergency facilities that are capable of treating the patient and extracting potential routes and routing times to the facilities based on the weighted conditions at the time the emergency request is made;

assigning, via a cloud on-demand self-service running on an application on a graphical-user interface that communicates with the cloud computing infrastructure, a patient who is on the restricted list of acceptable patients to the emergency facility at the time of the emergency request by calculating a minimal treatment time for the patient comprising a minimum combined time of a wait time at the emergency facility and a routing time to the emergency facility from a location of the emergency request, and assigning the patient to the emergency facility having the minimum combined time with treatment capability for the emergency request based on the capability of each emergency facility;

determining wait times comprises factoring the severity of the emergency request and the number of patients in a queue at the emergency facility;

cross-checking assigned emergency facilities with the necessary capabilities to treat the patient from the database and confirming the emergency facility having the capabilities for the emergency request has combined minimum wait time, routing time and treatment capability;

facilitating information exchange with the emergency facility, via the cloud computing infrastructure after assigning the patient to the emergency facility while the patient is in-route to the emergency facility;

iteratively re-computing the minimal treatment time at a second time for each new emergency request for a new patient based on new emergency treatment request after the minimal treatment time was calculated at the time of the emergency request;

wherein the treatment request feeds back to update the wait times based on the patient potentially receiving care while in the medical transportation vehicle;

wherein the assigning re-assigns the patient and each new patient based on the recomputed minimal treatment time considering the severity level of the patient and the number of patients in each queue;

wherein the minimal treatment time is optimized for the patient by the assigning a weighted sum of the wait times of all patients that requested medical services, wherein the minimal treatment time is calculated by using a weighted bipartite assignment having a set of edges connecting vertices from a set of patients to vertices belonging to a set of time-slots in the emergency facilities such that each vertex appears at most once and a sum of the weights of selected edges is a maximum, and wherein the routing time starts at the time of the emergency request, further comprising triggering, via the cloud on-demand self-service running on the application on the graphical-user interface that communicates with the cloud computing environment, a treatment request at the emergency facility to place the patient in a wait time queue a priori according to the patient being assigned to the emergency facility with the minimal treatment time, wherein the database including the information further including a second restricted list of authorized patients for a medical insurance accepted at the emergency facilities, the second restricted list being a subset of the first restricted list, wherein the assigning calculates the routing time to the emergency facility according to traffic data and a minimization of a time to reach the emergency facility based on the traffic data, wherein the wait time at the emergency facility used in the calculating the minimal treatment time is adjusted according to a weighted severity of the emergency request; and creating and assigning the patient into an integrated routing plan to an appropriate emergency facility by feeding the data collected from the database, the facilities, traffic conditions, routes into an algorithm which assigns each patient and integrated routing plan to an appropriate emergency facility with the best treatment time.

\* \* \* \* \*